United States Patent [19]

Carlson

[11] 4,115,101
[45] Sep. 19, 1978

[54] 1-ARYL-4-PYRIDONES
[75] Inventor: Glenn R. Carlson, North Wales, Pa.
[73] Assignee: Rohm and Haas Company, Philadelphia, Pa.
[21] Appl. No.: 815,971
[22] Filed: Jul. 15, 1977

Related U.S. Application Data

[62] Division of Ser. No. 689,219, May 24, 1976, Pat. No. 4,051,142.
[51] Int. Cl.$^2$ .................. A01N 9/22; C07D 213/55; C07D 213/56; C07D 213/57
[52] U.S. Cl. ....................... 71/94; 260/295.5 R; 260/295.5 A; 260/294.9; 260/345.7 R
[58] Field of Search ............. 71/94; 260/295.5 R, 260/294.9, 295.5 A

[56] References Cited
U.S. PATENT DOCUMENTS

| 3,503,986 | 3/1970 | Seidel et al. | 260/294.9 |
|---|---|---|---|
| 3,576,814 | 4/1971 | Siedel et al. | 260/295.5 T |
| 3,711,488 | 1/1973 | Bayer et al. | 260/295.5 R |
| 3,761,240 | 9/1973 | Seidel et al. | 71/94 |
| 4,028,084 | 6/1977 | McNulty et al. | 71/94 |

Primary Examiner—Alan L. Rotman
Attorney, Agent, or Firm—William E. Lambert, III; George W. F. Simmons

[57] ABSTRACT

Compounds of the formula

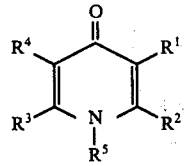

wherein
$R^1$ is carboxy, carboxylate, carbalkoxy, carbamoyl or cyano,
$R^2$ is alkyl,
$R^3$ is hydrogen or alkyl,
$R^4$ is hydrogen, alkyl, or halogen and
$R^5$ is phenyl or substituted phenyl, are active as plant growth regulators, and particularly as chemical hybridization agents.

13 Claims, No Drawings

1-ARYL-4-PYRIDONES

This is a division of application Ser. No. 689,219, filed May 24, 1976, now U.S. Pat. No. 4,051,142.

This invention relates to novel compounds which show activity as plant growth regulators, particularly as chemical hybridization agents, to growth regulant compositions which comprise these compounds, and to methods of regulating the growth of plants, particularly by inducing selective male sterility, with these compounds and compositions.

The cereal grains, such as corn, wheat, rice, rye, barley, millets, sorghum, and teff are among the major food crops throughout the world. This importance has led to extensive research to improve both the productivity and food value of these crops. One of the most important approaches taken to improve the quality and yield of the cereal grains has been hybridization. While hybridization has been an effective technique for some crops, most notably corn, there have been a number of problems with present techniques. For example, corn hybridization requires time-consuming hand detasseling or inefficient mechanical detasseling, possibly injuring the corn plant. Corn, barley, and wheat hybridization by means of cytoplasmic male sterile varieties can only be done with a limited genetic base, requiring a maintainer line and a restorer line. Furthermore, cytoplasmic male sterile techniques with barley and wheat necessitate a highly sophisticated approach to deal with the genetic complexities of these crops, and great success has not yet been achieved in developing a suitable approach. Since the induction of selective male sterility by chemical means would obviate many of the problems confronting the present hybridization techniques, new compounds which produce the desired sterility would be extemely desirable in dependably and economically supplying the male sterile plants needed for hybridization.

A new class of compounds has now been found which can be used to induce male sterility in cereal grains. The compounds of the invention are 4-pyridones having the formula

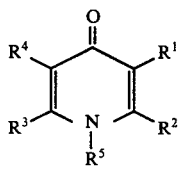

(I)

wherein
- $R^1$ is a carboxy group (—COOH) or an agronomically-acceptable salt thereof, a carbalkoxy group (—COOR, wherein R is an alkyl group, preferably having up to 12 carbon atoms, most preferably up to 4 carbon atoms), a carbamoyl group (—CONH$_2$), an alkyl or dialkyl carbamoyl group (—CONHR or —CONR$_2$), or a cyano group,
- $R^2$ is an alkyl group, preferably having up to 4 carbon atoms,
- $R^3$ is a hydrogen atom or an alkyl group, preferably having up to 4 carbon atoms,
- $R^4$ is a hydrogen atom, an alkyl group, preferably having up to 4 carbon atoms, or a halogen atom, preferably a bromine or a chlorine atom, and
- $R^5$ is a phenyl group or a substituted phenyl group, preferably having up to three substituents having a total of up to 6 carbon atoms.

In a preferred embodiment of the invention, $R^1$ is a carboxy group or a salt thereof, $R^2$ is a methyl group, $R^3$ is a hydrogen atom or a methyl group, $R^4$ is a hydrogen atom or a halogen atom, and $R^5$ is a substituted phenyl group.

When $R^1$ is a salt of a carboxy group, an alkali metal, alkaline earth metal, or transition metal can provide the cation. The cation can also be ammonium or substituted ammonium. Representative metal salt cations include alkali metal cations, such as sodium, potassium, lithium, or the like, alkaline earth metal cations, such as calcium, magnesium, barium, strontium, or the like, or heavy metal cations, such as zinc, manganese, cupric, cuprous, ferric, ferrous, titanium, aluminum, or the like. Among the ammonium salts are those in which the ammonium cation has the formula $NZ^1Z^2Z^3Z^4$, wherein each of $Z^1$, $Z^2$, $Z^3$, and $Z^4$ is individually a hydrogen atom, a hydroxy group, a ($C_1$–$C_4$)alkoxy group, a ($C_1$–$C_{20}$)alkyl group, a ($C_3$–$C_8$)alkenyl group, a ($C_3$–$C_8$)alkynyl group, a ($C_2$–$C_8$)hydroxyalkyl group, a ($C_2$–$C_8$)alkoxyalkyl group, a ($C_2$–$C_6$)aminoalkyl group, a ($C_2$–$C_6$)haloalkyl group, a substituted or unsubstituted phenyl group, a substituted or unsubstituted phenylalkyl group, having up to 4 carbon atoms in alkyl moiety, an amino or alkyl-substituted amino group, or any two of $Z^1$, $Z^2$, $Z^3$, or $Z^4$ can be taken together to form with the nitrogen atom a 5- or 6-member heterocyclic ring, optionally having up to one additional hetero oxygen, nitrogen, or sulfur atom in the ring, and preferably saturated, such as piperidine, morpholine, pyrrolidine, or piperazine ring, or the like, or any three of $Z^1$, $Z^2$, $Z^3$, or $Z^4$ can be taken together to form with the nitrogen atom a 5- or 6-member aromatic heterocyclic ring, such as a piperazole or pyridine ring. When the ammonium group contains a substituted alkyl, substituted phenyl or substituted phenylalkyl group, the substituents will generally be selected from halogen atoms, ($C_1$–$C_8$)alkyl groups, ($C_1$–$C_4$)alkoxy groups, hydroxy groups, nitro groups, trifluoromethyl groups, cyano groups, amino groups, ($C_1$–$C_4$)alkylthio groups, and the like. Such substituted phenyl groups preferably have up to two such substituents. Representative ammonium cations include ammonium, dimethylammonium, 2-ethylhexylammonium, bis(2-hydroxyethyl)-ammonium, tris(2-hydroxyethyl)ammonium, dicyclohexylammonium, t-octylammonium, 2-hydroxyethylammonium, morpholinium, piperdinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, diallylammonium, pyrazolium, propargylammonium, dimethylhydrazinium, hydroxyammonium, methoxyammonium, dodecylammonium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like.

Among the substituents which $R^5$ can contain are alkyl groups, preferably having up to 4 carbon atoms, aryl groups, preferably phenyl or substituted phenyl groups, alkyloxy groups, preferably having up to 4 carbon atoms, phenoxy or substituted phenoxy groups, halogen atoms, such as fluorine, chlorine, bromine, and iodine atoms, nitro groups, perhaloalkyl groups, such as trifluoromethyl groups, alkoxyalkyl groups, preferably having up to 6 carbon atoms, alkoxyalkoxy groups, preferably having up to 6 carbon atoms, amino groups, akyl or dialkyl amino groups, preferably having up to 4 carbon atoms in each alkyl substituent, cyano groups, carbalkoxy groups, preferably having up to 4 carbon atoms in the alkoxy moiety, carbamoyl groups, alkyl or dialkyl carbamoyl groups, preferably having up to 4 carbon atoms in each alkyl substituents, sulfo groups, sulfonamide groups, alkylcarbonyl or carboxylakyl groups, preferably having up to 4 carbon atoms in the alkyl moiety, alkanoyloxy groups, preferably having up to 4 carbon atoms, haloalkyl groups, alkanoylamido groups, preferably having up to 4 carbon atoms, alkylthio groups, preferably having up to 4 carbon atoms, alkylsulfinyl groups, preferably having up to 4 carbon atoms, alkylsulfonyl groups, preferably having up to 4 carbon atoms, and the like. The preferred substituents are halogen atoms, $(C_1-C_4)$alkyl groups, $(C_1-C_4)$-alkoxy groups, trifluoromethyl groups, and nitro groups.

Typical compounds within the scope of this invention include:

N-(4-chlorophenyl)-2,6-dimethylpyrid-4-one-3-carboxylic acid
N-(3-chlorophenyl)-2,6-dimethylpyrid-4-one-3-carboxylic acid
N-(3-bromophenyl)-2,6-dimethylpyrid-4-one-3-carboxylic acid
N-(2-chlorophenyl)-2,6-dimethylpyrid-4-one-3-carboxylic acid
N-(2-iodophenyl)-2,6-dimethylpyrid-4-one-3-carboxylic acid
N-(2-fluorophenyl)-2,6-dimethylpyrid-4-one-3-carboxylic acid
N-(4-fluorophenyl)-2,6-dimethylpyrid-4-one-3-carboxylic acid
N-(4-trifluoromethylphenyl)-2,6-dimethylpyrid-4-one-3-carboxylic acid
N-(4-methoxyphenyl)-2,6-dimethylpyrid-4-one-3-carboxylic acid
N-(3-nitrophenyl)-2,6-dimethylpyrid-4-one-3-carboxylic acid
N-(4-cyanophenyl)-2,6-dimethylpyrid-4-one-3-carboxylic acid
N-(4-chlorophenyl)-2-methylpyrid-4-one-3-carboxylic acid
N-(4-nitrophenyl)-2-methylpyrid-4-one-3-carboxylic acid
N-(4-cyanophenyl)-2,6-dimethylpyrid-4-one-3-carboxylic acid
N-(3-ethoxyphenyl)-2-methylpyrid-4-one-3-carboxylic acid
N-(4-methylphenyl)-2-methylpyrid-4-one-3-carboxylic acid
N-(3,4-dichlorophenyl)-2-methylpyrid-4-one-3-carboxylic acid
N-(4-methyl-3-chlorophenyl)-2-methylpyrid-4-one-3-carboxylic acid
N-(4-chlorophenyl)-2,5,6-trimethylpyrid-4-one-3-carboxylic acid
5-bromo-N-(4-chlorophenyl)-2,6-dimethylpyrid-4-one-3-carboxylic acid
5-bromo-N-(4-fluorophenyl-2,6-dimethylpyrid-4-one-3-carboxylic acid
5-chloro-N-(2,4-dichlorophenyl)-2,6-dimethylpyrid-4-one-3-carboxylic acid
5-fluoro-N-(3-chlorophenyl)-2,6-dimethylpyrid-4-one-3-carboxylic acid
5-bromo-N-(4-trifluoromethylphenyl)-2-methylpyrid-4-one-3-carboxylic acid and agronomically-acceptable salts of the above acids, N-(4-chlorophenyl)-3-carbomethoxy-2,6-dimethylpyrid-4-one
N-(4-fluorophenyl)-3-carbethoxy-2,6-dimethylpyrid-4-one
N-(3-methylphenyl)-3-carbobutoxy-2,6-dimethylpyrid-4-one
N-(3,4-dichlorophenyl)-3-carbethoxy-2-methylpyrid-4-one
N-phenyl-3-carbmethoxy-2-methylpyrid-4-one
N-(3-trifluoromethylphenyl)-3-cyano-2,6-dimethylpyrid-4-one
N-(4-chlorophenyl)-3-carbamoyl-2,6-dimethylpyrid-4-one
N-(2-methylphenyl)-3-methylcarbamoyl-2-methylpyrid-4-one
5-bromo-N-(4-chlorophenyl)-3-dimethylcarbamoyl-2,6-dimethylpyrid-4-one, and the like.

The compounds of the invention can be prepared by several convenient preparative routes. In the first method, a 4-hydroxy-2-pyrone of the formula

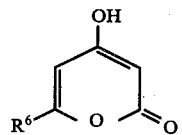 (II)

wherein $R^6$ is a hydrogen atom or an alkyl group, is reacted with an acid chloride of the formula

 $R^7COCl$ (III)

wherein $R^7$ is an alkyl group, in the presence of a suitable acylation catalyst such as trifluoroacetic acid, or the like. The product 3-alkylcarbonyl-4-hydroxy-2-pyrone is then treated with a strong acid, such as concentrated sulfuric acid, phosphoric acid, polyphosphoric acid, methanesulfonic acid, trifluoroacetic acid, or the like, to yield a 3-carboxy-4-pryone of the formula

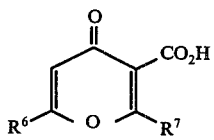 (IV)

wherein $R^6$ and $R^7$ are as defined above. This reaction is usually run at a temperature of about 0° to 100° C., using the acid itself as the solvent. The 3-carboxy-4-pyrone is then esterified with a suitable alcohol, preferably a $(C_1-C_4)$-alkanol. One convenient technique is a Fischer esterification, using anhydrous hydrochloric acid as a catalyst and the alcohol as the solvent. This esterification is generally carried out at about 35° to about 150° C., optionally using an inert cosolvent such as methylene chloride, ethylene chloride, diethyl ether, toluene, xylene, or the like. When $R^6$ is a methyl atom, an ester of the pyrone of Formula IV can be prepared directly from dehydroacetic acid by reaction with a strong acid, such as sulfuric acid, in an alcohol, such as methanol, with removal of water during the reaction. This reaction is generally carried out at a reflux temperature of the system.

A 3-carbalkoxy-4-pyridone of the formula

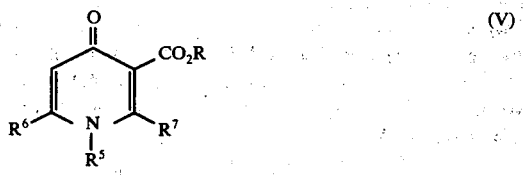

wherein R, $R^5$, $R^6$, and $R^7$ are as defined above is then prepared by reacting the 3-carbalkoxy-4-pyrone with an equimolar or excess amount of the amine of the formula

   (VI)

wherein $R^5$ is as defined above. This reaction is generally carried out in an inert solvent, such as toluene, xylene, benzene, chloroform, methylene chloride, or the like, at a temperature at which the water formed during the reaction can be removed by azeotropic distillation, using about 1 to 5% by weight of an acid catalyst such as p-toluenesulfonic acid, hydrochloric acid, sulfuric acid, methanesulfonic acid, or the like. The free acid, its salts, amides, and other esters can then be prepared by conventional techniques.

In a second method for preparing compounds of the invention, a β-haloacrylohalide of the formula

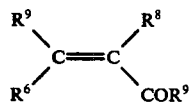   (VII)

wherein $R^6$ is as defined above, $R^8$ is a halogen atom or an alkyl group, and $R^9$ is a halogen atom, preferably a chlorine atom, is reacted with a β-ketoester salt of the formula

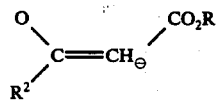   (VIII)

wherein R and $R^2$ are as defined above to yield a 3-carbalkoxy-4-pyrone of the formula

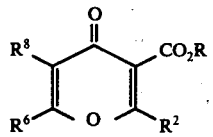   (IX)

wherein R, $R^2$, $R^6$, and $R^8$ are as defined above. In the initial step of this method, the β-ketoester salt is prepared by reacting the corresponding β-ketoester with a strong base, such as sodium hydroxide, potassium hydroxide, sodium hydride, potassium hydride, sodium methoxide, sodium t-butoxide, potassium methoxide, or the like in an inert solvent such as tetrahydrofuran, diethyl ether, benzene, toluene, heptane, or the like, at a temperature of about −20° to about 20° C. Generally without isolation, the anion is then reacted directly with the β-haloacrylohalide at a temperature of about 0° to about 150° C. The corresponding β-acetylacrylohalide can also be used in this reaction. The pyrone of Formula IX is then reacted with an amine of Formula VI by the same procedure outlined above to yield the corresponding 3-carbalkoxy-4-pyridone. The free acid, its salts, amides, and other esters can then be prepared by conventional techniques.

The compounds of the invention in which $R^4$ is a halogen atom can be prepared by reacting the corresponding 4-pyridones in which $R^4$ is a hydrogen atom with one equivalent of a halogenating agent such as bromine, chlorine, sulfuryl bromide, sulfuryl chloride, or the like in a suitable inert solvent such as ethylene dichloride, methanol, or the like.

The following examples will further illustrate the compounds of the invention and their preparation, but are not intended to limit the invention in any way. All temperatures are in degrees centigrade and parts and percentages are by weight, unless otherwise indicated. Specific illustrative preparations of the compounds of Examples 1, 2, 3, 4, 5, 35, and 36 are provided. Table I lists typical compounds of the invention and Table II lists their melting points and elemental analyses.

EXAMPLES 1 to 3

Preparation of N-(4-chlorophenyl)-3-carboxyl-2,6-dimethylpyrid-4-one, its methyl ester, and its sodium salt Method A a. 200 g of dehydroacetic acid is dissolved in 1000 g 85% $H_2SO_4$ and heated to 85° for 4 hours. The reaction is quenched in 2000 ml ice-water, and the water extracted with 3×300 ml of chloroform. After evaporation, the resulting solid is recrystallized twice from benzene to give 55–105 g of 3-carboxy-2,6-dimethylpyr-4-one (m.p. 98°).

b. 42 g of 3-carboxy-2,6-dimethylpyr-4-one is dissolved in 250 ml of methylene chloride. In a second flask, 20 ml of acetyl chloride is cautiously added to 400 ml of methanol. The two solutions are mixed and refluxed for 5 hours. Solid sodium carbonate is added and the solvent removed after a water wash. The residue is distilled (115°–125° at 0.1 mm) to give 40 g of 3-carbomethoxy-2,6-dimethylpyr-4-one as a waxy solid.

c. 40 g of 3-carbomethoxy-2,6-dimethylpyr-4-one and 30.2 g of 4-chloroaniline are dissolved in 400 ml of toluene along with 400 mg of p-toluenesulfonic acid monohydrate. The reaction mixture is refluxed for 4 hours. The solvent is removed and the product crystallized from ether to yield 30 g of N-(4-chlorophenyl)-3-carbomethoxy-2,6-dimethylpyrid-4-one (m.p. 189°–90°).

d. 16 g of N-(4-chlorophenyl)-3-carbomethoxy-2,6-dimethylpyrid-4-one is suspended in 450 g of 5% aqueous sodium hydroxide and stirred at room temperature for 24 hours. Acidification yields 14.2 g of N-(4-chlorophenyl)-3-carboxy-2,6-dimethylpyrid-4-one (m.p. 260°–61.5° decomp.) which is converted to its sodium salt (m.p. >310°) by neutralization with sodium hydroxide.

Method B 1.68 g of 2,6-dimethylpyr-4-one-3-carboxylic acid and 1.30 g of 4-chloroaniline are dissolved in 10 ml of benzene along with 120 mg of p-toluenesulfonic acid monohydrate. The reaction mixture is then refluxed for 2½ hours. Extraction with dilute base and acidification of the basic extracts yields 250 mg of N-(4-chlorophenyl)-2,6-dimethylpyrid-4-one-3-carboxylic acid.

Method C 100 g of dehydroacetic acid is added to a 1 liter 3-neck flask containing 500 ml of dry methanol and 25 g of 96% sulfuric acid. The flask is fitted with a magnetic stirring bar, thermometer and a Soxhlet extractor filled with 100 g of Linde-type 3A molecular sieves. The reaction mixture is brought to reflux, allowing the condensed solvent vapors to percolate through the sieves. After 30 hours, the reaction mixture is cooled, 250 ml of methylene chloride is added and the pH adjusted to 6 with aqueous sodium hydroxide. 400 ml of water is added causing a phase separation. The methylene chloride phase is collected and the aqueous phase is extracted with methylene chloride (1×200, 2×100 ml). The extracts are combined and backwashed with 400 ml of water. Evaporation of the solvent yields 90 g of crude 3-carbomethoxy-2,6-dimethylpyr-4-one which is purified by vacuum distillation. Yield of the purified material is 65 g (b.p. 131°-5° at 1.0 mm).

EXAMPLES 4 AND 5

Preparation of N-phenyl-3-carboxy-2,6-dimethylpyrid-4-one and its sodium salt a. 16.8 g of 3-carboxy-2,6-dimethylpyr-4-one and 18.5 g of aniline are dissolved in 150 ml methylene chloride along with 1.0 g p-toluenesulfonic acid monohydrate and gently refluxed for 24 hours. Extraction with dilute base and acidification of the basic extracts yields 4 to 5 g of N-phenyl-3-carboxy-2,6-dimethylpyr-4-one (m.p. 274°-5°), which can be converted into a water soluble sodium salt (m.p. 212°, decomp.).

EXAMPLE 35

Preparation of 5-Bromo-N-(4-chlorophenyl)-2,6-dimethylpyrid-4-one-3-carboxylic acid and its sodium salt Sodium N-(4-chlorophenyl)-2,6-dimethylpyrid-4-one-3-carboxylate (3.0 g) is dissolved in 300 ml of dry methanol. A dilute methanolic bromine solution is added until a yellow color persists for 30 seconds after the addition of a single drop. A white precipitate forms which is dissolved in dilute base. The solution is filtered and reacidified to give 2.4 g of 5-bromo-N-(4-chlorophenyl)-2,6-dimethylpyrid-4-one-3-carboxylic acid (mp >200°, decomp) which is isolated as a white powder. This material is transformed into its sodium salt (mp >200° decomp), by neutralization with sodium hydroxide.

EXAMPLE 36

Preparation of N-phenyl-2-methylpyrid-4-one-3-carboxylic acid a. 6.5 g of acetoacetic ester (ethyl acetoacetate) is dissolved in 35 ml of dry tetrahydrofuran and slowly added via syringe to a three-neck flask containing 2.5 g of a 50% sodium hydride dispersion. The reaction flask is cooled in an ice bath and maintained under a nitrogen atmosphere throughout the addition. The resulting solution is then allowed to stand at 25° for about 1 hour prior to use.

6.2 g of trans-β-chloroacryloyl chloride is dissolved in 35 ml of dry tetrahydrofuran added dropwise to the reaction mixture over the course of 1½ hours while maintaining a temperature of 10 to 15. The reaction mixture is then allowed to stand at room temperature for 1½ hours, followed by 2 hours of reflux. The reaction mixture is then cooled and dumped into water and extracted several times with ether. Evaporation of the solvent yields 5.5 g of an oil containing 3-carboethoxy-2-methylpyr-2-one.

b. The crude 3-carboethoxy-2-methylpyr-4-one isolated from the previous reaction is dissolved in 50 ml toluene. 2.4 g of aniline and 400 mg of p-toluenesulfonic acid monohydrate are added and the mixture refluxed for 1 hour. Evaporation of the solvent leaves 6.3 g of crude 3-carboethoxy-N-phenyl-2-methylpyrid-4-one.

c. 6.3 g of crude 3-carboethoxy-N-phenyl-2-methylpyrid-4-one is suspended in 100 g of 5% aqueous sodium hydroxide and placed on a steambath for approximately 1 hour. The mixture is cooled, filtered and acidified to yield 2.3 g of N-phenyl-2-methylpyrid-4-one-3-carboxylic acid which is recrystallized from methylene chloride/ether (mp 203°-4°).

TABLE I

1-Aryl-4-Pyridones

| Example No. | R | $R^2$ | $R^3$ | $R^4$ | X |
|---|---|---|---|---|---|
| 1 | H | $CH_3$ | $CH_3$ | H | 4-Cl |
| 2 | Na | $CH_3$ | $CH_3$ | H | 4-Cl |
| 3 | $CH_3$ | $CH_3$ | $CH_3$ | H | 4-Cl |
| 4 | H | $CH_3$ | $CH_3$ | H | H |
| 5 | Na | $CH_3$ | $CH_3$ | H | H |
| 6 | Na | $CH_3$ | $CH_3$ | H | 3,4-diCl |
| 7 | H | $CH_3$ | $CH_3$ | H | 4-I |
| 8 | Na | $CH_3$ | $CH_3$ | H | 4-I |
| 9 | H | $CH_3$ | $CH_3$ | H | 4-Br |
| 10 | Na | $CH_3$ | $CH_3$ | H | 4-Br |
| 11 | H | $CH_3$ | $CH_3$ | H | 4-F |
| 12 | Na | $CH_3$ | $CH_3$ | H | 4-F |
| 13 | H | $CH_3$ | $CH_3$ | H | 4-$OCH_3$ |
| 14 | Na | $CH_3$ | $CH_3$ | H | 4-$OCH_3$ |
| 15 | H | $CH_3$ | $CH_3$ | H | 4-$CH_3$ |
| 16 | Na | $CH_3$ | $CH_3$ | H | 4-$CH_3$ |
| 17 | H | $CH_3$ | $CH_3$ | H | 4-$CF_3$ |
| 18 | Na | $CH_3$ | $CH_3$ | H | 4-$CF_3$ |
| 19 | H | $CH_3$ | $CH_3$ | H | 4-$NO_2$ |
| 20 | Na | $CH_3$ | $CH_3$ | H | 4-$NO_2$ |
| 21 | H | $CH_3$ | $CH_3$ | H | 3-Cl |
| 22 | Na | $CH_3$ | $CH_3$ | H | 3-Cl |
| 23 | H | $CH_3$ | $CH_3$ | H | 3-F |
| 24 | Na | $CH_3$ | $CH_3$ | H | 3-F |
| 25 | H | $CH_3$ | $CH_3$ | H | 2-Cl |
| 26 | Na | $CH_3$ | $CH_3$ | H | 2-Cl |
| 27 | H | $CH_3$ | $CH_3$ | H | 2-F |
| 28 | Na | $CH_3$ | $CH_3$ | H | 2-F |
| 29 | H | $CH_3$ | $CH_3$ | H | 3,4-di$CH_3$ |
| 30 | Na | $CH_3$ | $CH_3$ | H | 3,4-di$CH_3$ |
| 31 | H | $CH_3$ | $CH_3$ | H | 4-$CH_3$-3-Cl |
| 32 | Na | $CH_3$ | $CH_3$ | H | 4-$CH_3$-3-Cl |
| 33 | H | $CH_3$ | $CH_3$ | H | 2,4-diCl |
| 34 | Na | $CH_3$ | $CH_3$ | H | 2,4-diCl |
| 35 | Na | $CH_3$ | $CH_3$ | Br | 4-Cl |
| 36 | H | $CH_3$ | H | H | H |
| 37 | Na | $CH_3$ | H | H | H |
| 38 | H | $CH_3$ | $CH_3$ | Br | 4-F |
| 39 | Na | $CH_3$ | $CH_3$ | Br | 4-F |

TABLE I-continued

1-Aryl-4-Pyridones $$\text{structure: R}^4, \text{R}^3, \text{R}^2 \text{ substituted 4-pyridone with COOR group, N-aryl with X substituent}$$

| Example No. | R | $R^2$ | $R^3$ | $R^4$ | X |
|---|---|---|---|---|---|
| 40 | H | CH₃ | CH₃ | H | 3-Br |
| 41 | Na | CH₃ | CH₃ | H | 3-Br |
| 42 | H | CH₃ | CH₃ | H | 3-CF₃ |
| 43 | Na | CH₃ | CH₃ | H | 3-CF₃ |
| 44 | H | CH₃ | CH₃ | H | 2,4-diF |
| 45 | Na | CH₃ | CH₃ | N | 2,4-diF |
| 46 | H | CH₃ | H | H | 4-I |
| 47 | Na | CH₃ | H | H | 4-I |
| 48 | H | CH₃ | H | H | 4-Cl |
| 49 | Na | CH₃ | H | H | 4-Cl |
| 50 | H | CH₃ | H | H | 4-F |
| 51 | Na | CH₃ | H | H | 4-F |
| 52 | CH₃ | CH₃ | CH₃ | H | 4-F |
| 53 | H | CH₃ | CH₃ | Br | 3-F |
| 54 | H | CH₃ | CH₃ | Br | 4-Br |
| 55 | H | CH₃ | CH₃ | Br | 4-I |

TABLE II

1-Aryl-4-Pyridones
Physical Data

| Example No. | m.p. (° C) | | %C | %H | %N | %X |
|---|---|---|---|---|---|---|
| 1 | 260–261.5 | calc. | 60.55 | 4.36 | 5.04 | 12.77 |
| | | found | 58.75 | 4.22 | 5.05 | 14.51 |
| 2 | >310° (hydrate) | calc. | 53.02 | 4.13 | 4.44 | 11.18 |
| | | found | 54.45 | 4.03 | 4.48 | 11.23 |
| 3 | 189–90° | calc. | 61.76 | 4.83 | 4.80 | 12.15 |
| | | found | 61.30 | 4.84 | 4.82 | 12.28 |
| 4 | 274–5° | *** | | | | |
| 5 | 208° | calc. | 63.39 | 4.56 | 5.28 | — |
| | | found | 62.16 | 5.25 | 5.07 | — |
| 6 | 240° | calc. | 50.32 | 3.02 | 4.19 | 21.22 |
| | | found | 48.97 | 3.19 | 4.32 | 21.20 |
| 7 | 288° | calc. | 44.55 | 3.28 | 3.80 | 34.38 |
| | | found | 45.22 | 3.35 | 3.70 | 33.87 |
| 8 | >300° | calc. | 42.99 | 2.84 | 3.58 | 32.45 |
| | | found | 42.97 | 2.76 | 3.67 | 32.14 |
| 9 | 272–3° | calc. | 52.19 | 3.76 | 4.35 | 24.81 |
| | | found | 52.19 | 3.83 | 4.12 | 25.37 |
| 10 | >300° | calc. | 48.86 | 3.22 | 4.07 | 23.22 |
| | | found | 49.07 | 3.25 | 4.04 | 23.37 |
| 11 | 229–30° | calc. | 64.36 | 4.63 | 5.36 | 7.27 |
| | | found | 64.48 | 4.73 | 5.15 | 7.73 |
| 12 | >300° | calc. | 59.36 | 3.92 | 4.95 | 6.71 |
| | | found | 59.30 | 4.03 | 5.28 | 7.23 |
| 13 | 238–9° | calc. | 65.92 | 5.53 | 5.13 | — |
| | | found | 66.22 | 5.64 | 4.88 | — |
| 14 | 300° | calc. | 61.01 | 4.78 | 4.74 | — |
| | | found | 60.54 | 4.88 | 5.12 | — |
| 15 | 236–7.5° | calc. | 70.02 | 5.88 | 5.45 | — |
| | | found | 70.20 | 6.01 | 5.17 | — |
| 16 | 298° (hydrate) | calc. | 60.60 | 5.43 | 4.71 | — |
| | | found | 57.72 | 5.22 | 4.24 | — |
| 17 | 254–6° | calc. | 57.88 | 3.89 | 4.50 | 18.31 |
| | | found | 58.02 | 4.02 | 4.34 | 17.68 |
| 18 | 276–7° | calc. | 54.06 | 3.33 | 4.20 | 17.10 |
| | | found | 54.09 | 3.38 | 4.03 | 15.93 |
| 19 | 249–50° | calc. | 58.33 | 4.20 | 9.72 | — |
| | | found | 58.82 | 4.28 | 9.66 | — |
| 20 | >200° (hydrate) | calc. | 51.22 | 3.99 | 8.54 | — |
| | | found | 48.97 | 3.94 | 8.30 | — |
| 21 | 264–5° | calc. | 60.55 | 4.36 | 5.04 | 12.77 |
| | | found | 60.74 | 4.37 | 4.81 | 16.56 |
| 22 | 202° (hydrate) | calc. | 53.02 | 4.13 | 4.44 | 11.18 |
| | | found | 54.45 | 4.37 | 4.40 | 11.26 |
| 23 | 243–5° | calc. | 64.36 | 4.63 | 5.36 | 7.27 |
| | | found | 64.51 | 4.63 | 5.44 | 7.45 |
| 24 | 212–5° (hydrate) | calc. | 55.81 | 4.35 | 4.65 | 6.31 |
| | | found | 57.56 | 4.31 | 4.77 | 5.90 |
| 25 | 157.5–8.5° | calc. | 60.55 | 4.36 | 5.04 | 12.77 |
| | | found | 61.04 | 4.38 | 4.93 | 13.24 |
| 26 | 218° (hydrate) | calc. | 53.02 | 4.13 | 4.44 | 11.18 |
| | | found | 53.12 | 4.64 | 4.37 | 10.88 |
| 27 | 220–2° | calc. | 64.36 | 4.63 | 5.36 | 7.27 |
| | | found | 64.86 | 4.67 | 5.51 | 7.13 |
| 28 | 224–8 | calc. | 59.36 | 3.92 | 4.95 | 6.71 |
| | | found | 57.84 | 4.26 | 5.26 | 4.92 |
| 29 | 260–1.5° | calc. | 70.83 | 6.32 | 5.16 | — |
| | | found | 71.29 | 6.50 | 4.98 | — |
| 30 | 212° | calc. | 55.52 | 5.50 | 4.78 | — |
| | | found | 57.56 | 5.38 | 4.00 | — |
| 31 | 255.5–7° | calc. | 61.75 | 4.84 | 4.80 | 12.16 |
| | | found | 61.86 | 4.90 | 4.58 | 12.35 |
| 32 | 220–5° | calc. | 57.42 | 4.18 | 4.47 | 11.30 |
| | | found | 50.71 | 4.18 | 4.01 | 16.90 |
| 33 | 208.5–10° | calc. | 53.87 | 3.55 | 4.49 | 22.72 |
| | | found | 54.02 | 3.57 | 4.40 | 22.99 |
| 34 | 210° (hydrate) | calc. | 47.74 | 3.44 | 3.98 | 20.14 |
| | | found | 46.09 | 3.44 | 3.73 | 20.09 |
| 35 | >200° (hydrate) | calc. | 42.28 | 3.04 | 3.52 | — |
| | | found | 41.56 | 2.74 | 3.20 | — |
| 36 | 203–4° | calc. | 68.11 | 4.84 | 6.11 | — |
| | | found | 67.89 | 4.65 | 6.35 | — |
| 37 | 240° (hydrate) | calc. | 57.99 | 4.49 | 5.20 | — |
| | | found | 58.15 | 4.10 | 5.25 | — |
| 38 | 273–6° | calc. | 49.43 | 3.26 | 4.12 | 23.49 |
| | | found | 51.57 | 3.43 | 4.25 | 20.99 |
| 39 | — | *** | | | | |
| 40 | 261–2° | calc. | 52.19 | 3.76 | 4.35 | 24.81 |
| | | found | 52.64 | 3.87 | 4.47 | 24.50 |
| 41 | 232° | *** | | | | |
| 42 | 254–6° | calc. | 57.88 | 3.89 | 4.50 | 18.31 |
| | | found | 58.04 | 4.04 | 4.32 | 18.63 |
| 43 | 195–203° (hydrate) | *** | | | | |
| 44 | 203–6° | calc. | 60.21 | 3.97 | 5.02 | 13.61 |
| | | found | 60.36 | 4.18 | 4.89 | 13.37 |
| 45 | 199–209° | *** | | | | |
| 46 | 264–6° | calc. | 43.96 | 2.84 | 3.95 | 35.74 |
| | | found | 43.81 | 2.77 | 3.81 | 35.45 |
| 47 | 297° | *** | | | | |
| 48 | 259–61° | calc. | 59.21 | 3.82 | 5.31 | 13.45 |
| | | found | 58.98 | 3.88 | 5.17 | 13.72 |
| 49 | 290–92° | *** | | | | |
| 50 | 237–9° | calc. | 63.15 | 4.08 | 5.67 | 7.69 |
| | | found | 62.83 | 4.04 | 5.63 | 7.47 |
| 51 | 297–8° | *** | | | | |
| 52 | 209–11° | calc. | 65.44 | 5.13 | 5.09 | 6.90 |
| | | found | 65.01 | 5.16 | 5.00 | 6.73 |

***no elemental analysis performed

The compounds of the invention are particularly useful as chemical hybridization agents in cereal crops, such as wheat, barley, corn, rice, sorghum, millets, oats, rye and the like. When used as chemical hybridization agents, the compounds effectively induce a high degree of selective male sterility, that is without also inducing significant female sterility, in the treated plants and without causing significant growth inhibition of the treated plants. As used herein, the term male sterility includes both actual male sterility, as evidenced by a lack of male flower parts or by sterile pollen, and functional male sterility, in which the male flower parts are unable to cause pollination. The compounds of the invention also cause other plant growth regulatory responses, such as for example, control of flowering, control of fruiting and inhibition of seed formation in non-cereal species, and other related growth regulatory responses.

When used as plant growth regulators, the compounds of the invention are applied in any amount which will be sufficient to effect the desired plant response without causing any undesirable or phytotoxic response. For example, when the compounds of the invention are used as chemical hybridization agents, they are generally applied to the crops to be treated as a rate of about 1/32 to about 20 pounds per acre and preferably about ⅛ to about 10 pounds per acre. The rate of application will vary depending on the crop being treated, the compound being used for treatment, and related factors.

To obtain hybrid seed, the following procedure is generally employed. The two parents to be crossed are planted in alternate strips. The female parent is treated with a compound of the invention. The male-sterile female parent thus produced will be pollinated by pollen from the other, male-fertile, male parent, and the seed produced by the female parent will be hybrid seed which can then be harvested by conventional means.

A preferred method of applying a compound of the invention as a chemical hybridization agent is by foliar application. When this method is employed, selective male sterility is most effectively induced when the compound is applied between flower initiation and meiosis. The compounds of the inventions may also be applied as a seed treatment by soaking the seed in a liquid formulation containing the active compound or by coating the seed with the compound. In seed treatement applications, the compounds of the invention will generally be applied at a rate of about ¼ to about 10 pounds per hundred weight of seed. The compounds of the invention are also effective when applied to the soil or to the water surface in rice crops.

The compounds of the invention can be used as plant growth regulators either individually or in mixtures. For example, they can be used in combination with other plant growth regulators, such as auxins, gibberellins, ethylene-releasing agents such as ethephon, pyridones, cytokinins, maleic hydrazide, succinic acid 2,2-dimethylhydrazide, choline and its salts, (2-chloroethyl) trimethylammonium chloride, triiodobenzoic acid, tributyl-2,4-dichlorobenzylphosphonium chloride, polymeric N-vinyl-2-oxazolidinones, tri(dimethylaminoethyl) phosphate and its salts, and N-dimethylamino-1,2,3,6-tetrahydrophthalamic acid and its salts, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no significant detrimental effect on the soil, equipment, crops, or agronomic environment. Mixtures of the compounds of the invention may also be used in any of these formulations. The compositions of the invention can be either solid or liquid formulations or solutions. For example, the compounds can be formulated as wettable powders, emulsifiable concentrates, dusts, granular formulations, aerosols, or flowable emulsion concentrates. In such formulations, the compounds are extended with a liquid or solid carrier and, when desired suitable surfactants are incorported.

It is usually desirable, particularly in foliar applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% by weight with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent or surfactant which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates of usually about 10% to 60% by weight and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent may generally constitute about 0.5% to about 3% by weight of the composition, and a wetting agent may generally constitute from about 0.1% to about 5% by weight of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% by weight use concentration.

Granular formulations can be prepared by impregnating a solid such as granular fuller's earth, vermiculite, ground corn cobs, seed nulls, including bran or other grain hulls, or similar material. A solution of one or more of the compounds in a volatile organic solvent can be sprayed or mixed with the granular solid and the solvent then removed by evaporation. The granular material can have any suitable size, with a preferably size range of 16 to 60 mesh. The active compound will usually comprise about 2 to 15% by weight of the granular formulation.

Salts of the compounds of the invention can be formulated and applied as aqueous solutions. The salt will typically comprise about 0.05 to about 50% by weight, preferably about 0.1% to about 10%, of the solution.

These compositions can also be further diluted with water if desired prior to actual application. In some applications, the activity of these compositions can be enhanced by incorporating into the composition an adjuvant such as glycerin, methylethylcellulose, hydroxyethylcellulose, polyoxyethylenesorbitan monooleate, polypropylene glycol, polyacrylic acid, polyethylene sodium malate, polyethylene oxide, or the like. The adjuvant will generally comprise about 0.1 to about 5% by weight, preferably about 0.5 to about 2%, of the composition. Such compositions can also optionally include an agronomically-acceptable surfactant.

The compounds of the invention can be applied as sprays by methods commonly employed, such as conventional hydraulic sprays, aerial sprays, and dusts. For low-volume applications a solution of the compound is usually used. The dilution and volume of application will usually depend upon such factors as the type of equipment employed, the method of application, the area to be treated and the type and stage of development of the crop being treated.

The following examples will further illustrate the growth regulatory activity of the compounds of the invention but are not intended to limit the invention in any way.

EXAMPLE 56

Chemical Hybridization Activity

The following procedures are used to evaluate the activity of the compounds of the invention for inducing male sterility in cereals.

An awned variety (Fielder) and an awnless variety (Mayo-64) of spring wheat are planted at the rate of 6 to 8 seeds per 6 inches pot containing a sterile medium of 3 parts soil and 1 part humus. The plants are grown under short-day (9 hour) conditions for the first 4 weeks to obtain good vegetative growth before flower initiation. The plants are then moved to long-day (16 hour) conditions which are provided by high intensity lights in the greenhouse. The plants are fertilized at 2, 4, and 8 weeks after planting with a water soluble fertilizer (16-25-16) at the rate of 1 tsp/gal of water, and are frequently sprayed with isotox for aphid control and dusted with sulfur for powdery mildew control.

Test compounds are foliarly applied to the awned female plants when these plants reach the flag leaf emergence stage (stage 8 on Feekes' scale). All compounds are applied in a carrier volume of 50 gal/A containing a surfactant, such as Triton X-100 at the rate of 2 oz/50 gal.

After spike emergence but before anthesis, 4 to 6 spikes per pot are bagged to prevent outcrossing. At the first signs of flower opening, two spikes per pot are cross pollinated, using the approach method, with the awnless male parent. As soon as the seeds became plainly visible, spike length is measured and seeds per spikelet counted in both bagged and crossed spikes. Male sterility can then be calculated as percent inhibition of seed set in bagged spikes of treated plants, and female fertility in crossed spikes can be calculated as percent of control seed set. After maturity the seed on crossed spikes are planted for determination of percent hybridization.

Percent sterility, percent fertility, and percent height inhibition are calculated from the following formulas:

a. % Sterility $= (S_c - S_t/S_c) \times 100$ $S_c$ = seeds/spikelet in bagged spikes of control plants $S_t$ = seeds/spikelet in bagged spikes of treated plants b. % Fertility $= (F_t/F_c) \times 100$ $F_t$ = seeds/spikelets in approach crossed spikes of treated plants $F_c$ = seeds/spikelet in unbagged spikes of control plants c. % Height inhibition $= (H_c - H_t/H_c) \times 100$ $H_c$ = height of control plants $H_t$ = height of treated plants Table III summarizes typical results obtained in the evaluation of compounds of the invention. A dash indicates that no determination of value was made.

TABLE III

| | Male Sterility, Fertility and Spike Length Inhibition | | | |
|---|---|---|---|---|
| Ex. No. | Rate (lb/A). | Male Sterility (%) | Fertility (% of CK) | Spike Length (% Inhibition) |
| 1 | ½ | 12 | — | 0 |
|  | 1 | 21 | — | 0 |
|  | 2 | 68 | 82 | 8 |
|  | 4* | 65 | 100 | 0 |
| 2 | ½ | 3 | — | 0 |
|  | 1 | 22 | 1 | 0 |
|  | 2 | 65 | 93 | 2 |
|  | 4 | 81 | 94 | 0 |
| 3 | ½ | 7 | — | 0 |
|  | 1 | 18 | — | 3 |
|  | 2 | 6 | — | 1 |
|  | 4 | 8 | — | 0 |
| 5 | ½ | 5 | — | 0 |
|  | 1 | 12 | — | 0 |
|  | 2 | 53 | 81 | 0 |
|  | 4 | 56 | 75 | 3 |
| 6 | ½ | — | — | — |
|  | 1 | 12 | — | 4 |
|  | 2 | 7 | 79 | 6 |
|  | 4 | 26 | 79 | 10 |
| 7 | 1 | 0 | — | 0 |
|  | 2 | 0 | — | 4 |
|  | 4 | 3 | — | 3 |
|  | 8 | 21 | — | 0 |
| 8 | 1 | 0 | — | 0 |
|  | 2 | 4 | — | 0 |
|  | 4 | 57 | — | 0 |
|  | 8 | 100 | — | 0 |
| 9 | 1 | 73 | — | 0 |
|  | 2 | 97 | — | 0 |
|  | 4 | 100 | — | 3 |
|  | 8 | 100 | — | 0 |
| 10 | 1 | 59 | — | 0 |
|  | 2 | 68 | — | 0 |
|  | 4 | 100 | — | 0 |
|  | 8 | 100 | — | 0 |
| 11 | 1 | 59 | — | 0 |
|  | 2 | 95 | — | 0 |
|  | 4 | 100 | — | 0 |
|  | 8 | 100 | — | 0 |
| 12 | 1 | 81 | — | 8 |
|  | 2 | 91 | — | 0 |
|  | 4 | 100 | — | 0 |
|  | 8 | 100 | — | 0 |
| 13 | 1 | 9 | — | 8 |
|  | 2 | 0 | — | 1 |
|  | 4 | 10 | — | 5 |
|  | 8 | 8 | — | 12 |
| 14 | 1 | 0 | — | 0 |
|  | 2 | 23 | — | 0 |
|  | 4 | 50 | — | 1 |
|  | 8 | 32 | — | 0 |
| 15 | 1 | 26 | — | 0 |
|  | 2 | 19 | — | 0 |
|  | 4 | 39 | — | 0 |
|  | 8 | 73 | — | 0 |
| 16 | 1 | 21 | — | 10 |
|  | 2 | 9 | — | 0 |
|  | 4 | 31 | — | 7 |
|  | 8 | 68 | — | 0 |
| 17 | 1 | 50 | — | 0 |
|  | 2 | 83 | — | 0 |
|  | 4 | 93 | — | 0 |
|  | 8 | 100 | — | 0 |
| 18 | 1 | 45 | — | 3 |
|  | 2 | 93 | — | 0 |
|  | 4 | 100 | — | 0 |
|  | 8 | 100 | — | 0 |

TABLE III-continued

Male Sterility, Fertility and Spike Length Inhibition

| Ex. No. | Rate (lb/A). | Male Sterility (%) | Fertility (% of CK) | Spike Length (% Inhibition) |
|---|---|---|---|---|
| 19 | 1 | 2 | — | 0 |
|  | 2 | 0 | — | 0 |
|  | 4 | 11 | — | 0 |
|  | 8 | 17 | — | 0 |
| 20 | 1* | 31 | — | 1 |
|  | 2* | 10 | — | 0 |
|  | 4* | 25 | — | 0 |
|  | 8* | 18 | — | 0 |
| 21 | 1 | 83 | — | 0 |
|  | 2 | 86 | — | 0 |
|  | 4 | 87 | — | 0 |
|  | 8 | 100 | — | 5 |
| 22 | 1 | 80 | — | 5 |
|  | 2 | 100 | — | 0 |
|  | 4 | 100 | — | 0 |
|  | 8 | 100 | — | 0 |
| 23 | 1 | 32 | — | 0 |
|  | 2 | 94 | 56 | 0 |
|  | 4 | 100 | 60 | 0 |
|  | 8 | 100 | 7 | 0 |
| 24 | 1 | — | — | — |
|  | 2 | — | — | — |
|  | 4 | 8 | — | 2 |
|  | 8 | 20 | — | 0 |
| 25 | 1 | 9 | — | 0 |
|  | 2 | 25 | — | 0 |
|  | 4 | 42 | — | 0 |
|  | 8 | 55 | — | 0 |
| 26 | 1 | 35 | — | 0 |
|  | 2 | 56 | — | 0 |
|  | 4 | 56 | — | 0 |
|  | 8 | 96 | — | 0 |
| 27 | ¼ | 15 | — | 1 |
|  | ½ | 26 | — | 2 |
|  | 1 | 0 | 100 | 0 |
|  | 2 | 10 | 100 | 0 |
| 28 | ¼ | 3 | — | 2 |
|  | ½ | 3 | — | 0 |
|  | 1 | 2 | 82 | 2 |
|  | 2 | 16 | 93 | 6 |
| 29 | 1 | 3 | — | 0 |
|  | 2 | 4 | — | 0 |
|  | 4 | 6 | — | 0 |
|  | 8 | 12 | — | 0 |
| 30 | 1 | 0 | — | 0 |
|  | 2 | 1 | — | 0 |
|  | 4 | 7 | — | 0 |
|  | 8 | 6 | — | 0 |
| 31 | 1 | 20 | — | 7 |
|  | 2 | 0 | — | 0 |
|  | 4 | 15 | — | 0 |
|  | 8 | 27 | — | 0 |
| 32 | 1 | 18 | — | 0 |
|  | 2 | 16 | — | 0 |
|  | 4 | 20 | — | 11 |
|  | 8 | 26 | — | 0 |
| 33 | 1 | 10 | — | 0 |
|  | 2 | 10 | — | 0 |
|  | 4 | 53 | — | 8 |
|  | 8** | 38 | — | 0 |
| 34 | 1 | 8 | — | 0 |
|  | 2 | 5 | — | 0 |
|  | 4 | 56 | — | 4 |
|  | 8 | 57 | — | 0 |
| 35 | 1 | 100 | — | 0 |
|  | 2 | 100 | — | 0 |
|  | 4 | 100 | — | 0 |
|  | 8 | 100 | — | 0 |
| 36 | ½ | 4 | — | 1 |
|  | 1 | 4 | — | 2 |
|  | 2 | 0 | — | 0 |
|  | 4 | 3 | — | 7 |
| 37 | ½ | 21 | — | 1 |
|  | 1 | 13 | — | 5 |
|  | 2 | 11 | — | 4 |
|  | 4 | 11 | — | 3 |
| 40 | ½ | 4 | 100 | 2 |
|  | 1 | 51 | 100 | 4 |
|  | 2 | 100 | 91 | 6 |
|  | 4 | 100 | 100 | 5 |
| 41 | ½ | 0 | — | 0 |
|  | 1 | 0 | — | 0 |
|  | 2 | 26 | 100 | 5 |
|  | 4 | 85 | 100 | 1 |
| 42 | ½ | 3 | — | 1 |
|  | 1 | 21 | 100 | 0 |
|  | 2 | 89 | 98 | 4 |
|  | 4 | 74 | 86 | 0 |
| 43 | ½ | 0 | — | 0 |
|  | 1 | 19 | 98 | 0 |
|  | 2 | 23 | 92 | 4 |
|  | 4 | 77 | 99 | 2 |

*phytotoxic
**incomplete soluability

It is to be understood that changes and variations may be made without departing from the spirit and scope of the invention as defined by the appended claims.

I claim:

1. A method of inducing male sterility in a cereal grain plant which comprises treating the plant prior to meiosis with an amount effective to produce male sterility in the plant of a compound of the formula

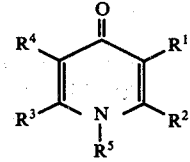

wherein
$R^1$ is a carboxy group or an agronomically-acceptable salt thereof, a carb($C_1$-$C_4$)alkoxy group, a carbamoyl group, a ($C_1$-$C_4$)alkyl or di($C_1$-$C_4$)alkyl carbamoyl group, or a cyano group,
$R^2$ is a ($C_1$-$C_4$)alkyl group,
$R^3$ is a hydrogen atom or a ($C_1$-$C_4$)alkyl group,
$R^4$ is a hydrogen atom, a ($C_1$-$C_4$)alkyl group, or a halogen atom, and
$R^5$ is an unsubstituted phenyl group or a substituted phenyl group having up to three substituents having a total of up to 6 carbon atoms.

2. A method of producing hybrid cereal grain seed which comprises treating a female parent of the cereal grain prior to meiosis with a compound of the formula

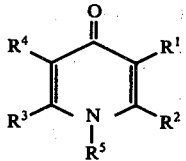

wherein
$R^1$ is a carboxy group or an agronomically-acceptable salt thereof, a carb($C_1$-$C_4$)alkoxy group, a carbamoyl group, a ($C_1$-$C_4$)alkyl or di($C_1$-$C_4$)alkyl carbamoyl group, or a cyano group,
$R^2$ is a ($C_1$-$C_4$)alkyl group
$R^3$ is a hydrogen atom or a ($C_1$-$C_4$)alkyl group,
$R^4$ is a hydrogen atom, a ($C_1$-$C_4$)alkyl group, or a halogen atom, and
$R^5$ is a phenyl group or a substituted phenyl group having up to three substituents having a total of up to 6 carbon atoms,
in an amount sufficient to produce male sterility in the female parent, causing the female parent to be pollinated with pollen from a male parent of the cereal grain, allowing the female parent to mature until seed formation is substantially complete, and harvesting the mature seed from the female parent.

3. A composition for inducing sterility in cereal grain plants which comprises an effective amount of a compound of the formula

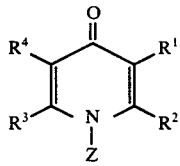

wherein
- $R^1$ is a carboxy group or an agronomically-acceptable salt thereof, a carb($C_1$-$C_4$)alkoxy group, a carbamoyl group, a ($C_1$-$C_4$)alkyl or di($C_1$-$C_4$)-alkyl carbamoyl group, or a cyano group,
- $R^2$ is a ($C_1$-$C_4$)alkyl group,
- $R^3$ is a hydrogen atom or a ($C_1$-$C_4$)alkyl group,
- $R^4$ is a hydrogen atom, a ($C_1$-$C_4$)alkyl group, or a halogen atom, and
- Z is a substituted phenyl group having up to three substituents selected from halogen atoms, ($C_1$-$C_4$)alkyl groups, ($C_1$-$C_4$)alkoxy groups, trifluoromethyl groups, and nitro groups, or, when $R^3$ is a hydrogen atom, additionally an unsubstituted phenyl group, and an agronomically-acceptable carrier.

4. The method of claim 1 wherein $R^1$ is a carboxy group or an agronomically-acceptable salt thereof.

5. The method of claim 4 wherein $R^2$ is a methyl group and $R^4$ is a hydrogen atom.

6. The method of claim 5 wherein $R^3$ is a methyl group.

7. The method of claim 6 wherein Z is a halophenyl group.

8. The method of claim 7 wherein Z is a 4-halophenyl group.

9. The method of claim 7 wherein Z is a 3-halophenyl group.

10. The method of claim 6 wherein Z is a trifluoromethylphenyl group.

11. The method of claim 5 wherein $R^3$ is a hydrogen atom.

12. The method of claim 4 wherein $R^2$ is a methyl group and $R^4$ is a halogen atom.

13. The method of claim 12 wherein $R^3$ is a methyl group.

* * * * *